(12) United States Patent
Hannon et al.

(10) Patent No.: US 10,029,071 B2
(45) Date of Patent: Jul. 24, 2018

(54) URINARY CATHETERS HAVING VARYING FLEXIBILITY

(71) Applicant: Hollister Incorporated, Libertyville, IL (US)

(72) Inventors: David Hannon, Ballina (IE); Jerome A. Henry, Castlebar (IE); Michael G. Murray, Ballina (IE); Mitchell J. Weinstein, Deerfield, IL (US)

(73) Assignee: Hollister Incorporated, Livertyville, IL (US)

( * ) Notice: Subject to any disclaimer, the term of this patent is extended or adjusted under 35 U.S.C. 154(b) by 540 days.

(21) Appl. No.: 14/438,703

(22) PCT Filed: Mar. 12, 2013

(86) PCT No.: PCT/US2013/030428
§ 371 (c)(1),
(2) Date: Apr. 27, 2015

(87) PCT Pub. No.: WO2014/077881
PCT Pub. Date: May 22, 2014

(65) Prior Publication Data
US 2015/0297863 A1 Oct. 22, 2015

Related U.S. Application Data

(60) Provisional application No. 61/726,111, filed on Nov. 14, 2012.

(51) Int. Cl.
*A61M 25/00* (2006.01)
*B29C 47/00* (2006.01)
*B29L 23/00* (2006.01)

(52) U.S. Cl.
CPC .... *A61M 25/0054* (2013.01); *A61M 25/0009* (2013.01); *A61M 25/0013* (2013.01);
(Continued)

(58) Field of Classification Search
CPC .......... A61M 25/0009; A61M 25/0013; A61M 25/0017; A61M 25/0054
See application file for complete search history.

(56) References Cited

U.S. PATENT DOCUMENTS

| 623,022 | A | 4/1899 | Johnson |
| 4,280,500 | A | 7/1981 | Ono |

(Continued)

FOREIGN PATENT DOCUMENTS

| EP | 0738519 A1 | 10/1996 |
| EP | 738519 A1 | 10/1996 |

(Continued)

OTHER PUBLICATIONS

English Translation of 'FR 2 390 967'.*
(Continued)

*Primary Examiner* — Benjamin Klein
(74) *Attorney, Agent, or Firm* — Cook Alex Ltd.

(57) ABSTRACT

A urinary catheter has a body and an outer layer surrounding at least a portion of the body. The structure of the body is varied and non-uniform so as to impart a varying flexibility along the length of the catheter. The frame may be injection molded, while the outer layer may be extruded. The frame may also, or alternatively, have selected regions or portions that include planar or spiral cuts or a coiled filament or corrugations or a multifilament braid or weave or mesh to impart a desired flexibility profile. The flexibility profile of a male urinary catheter may include alternating rigid and flexible regions, with proximal and distal rigid regions being configured to be positioned within the bladder and penis, with two flexible regions separated by a rigid region positioned between the penis and bladder when the catheter is deployed within a male urethra.

19 Claims, 8 Drawing Sheets

(52) U.S. Cl.
CPC ..... *A61M 25/0017* (2013.01); *B29C 47/0009* (2013.01); *B29L 2023/00* (2013.01)

(56) References Cited

U.S. PATENT DOCUMENTS

| | | | |
|---|---|---|---|
| 4,564,361 A | | 1/1986 | Akiyama |
| 4,764,324 A | | 8/1988 | Burnham |
| 5,342,386 A | | 8/1994 | Trotta |
| 5,496,271 A | * | 3/1996 | Burton .................. A61B 18/18 604/101.05 |
| 5,736,094 A | | 4/1998 | van Muiden |
| 5,792,401 A | | 8/1998 | Burnham |
| 6,017,335 A | | 1/2000 | Burnham |
| 6,097,976 A | | 8/2000 | Yang et al. |
| 6,213,995 B1 | | 4/2001 | Steen et al. |
| 6,213,996 B1 | | 4/2001 | Steen et al. |
| 6,256,525 B1 | | 7/2001 | Yang et al. |
| 6,291,543 B1 | | 9/2001 | Shah |
| 6,743,831 B2 | | 6/2004 | Olsen |
| 6,881,209 B2 | | 4/2005 | Boatman et al. |
| 6,945,957 B2 | | 9/2005 | Freyman |
| 7,244,242 B2 | | 7/2007 | Freyman |
| 7,306,585 B2 | * | 12/2007 | Ross ...................... A61L 29/06 604/523 |
| 7,597,903 B2 | | 10/2009 | Rosinskya et al. |
| 7,674,421 B2 | | 3/2010 | Ross |
| 7,722,795 B2 | | 5/2010 | Boatman et al. |
| 7,744,619 B2 | | 6/2010 | Eidenschink |
| 7,780,627 B2 | | 8/2010 | Freyman |
| 7,815,627 B2 | * | 10/2010 | Von Oepen ........... A61M 25/10 604/525 |
| 2003/0069522 A1 | | 4/2003 | Jacobsen et al. |
| 2004/0087933 A1 | | 5/2004 | Lee et al. |
| 2004/0198864 A1 | | 10/2004 | Olsen |
| 2006/0263404 A1 | | 11/2006 | Nielsen et al. |
| 2007/0005041 A1 | | 1/2007 | Frassica et al. |
| 2007/0225688 A1 | | 9/2007 | Goodwin |
| 2008/0179208 A1 | | 7/2008 | Murray et al. |
| 2009/0202614 A1 | * | 8/2009 | Kaplan ............... A61L 27/3604 424/443 |

FOREIGN PATENT DOCUMENTS

| | | |
|---|---|---|
| EP | 1 839 697 | 3/2007 |
| EP | 2 106 821 A1 | 10/2009 |
| FR | 2 390 967 | 12/1978 |
| GB | 2 372 211 | 8/2002 |

OTHER PUBLICATIONS

Office Communication for European Patent Appl'n. 13 716 493.5, dated Jan. 17, 2017.
International Search Report and Written Opinion for PCT/US2013/030428, dated Aug. 9, 2013.

* cited by examiner

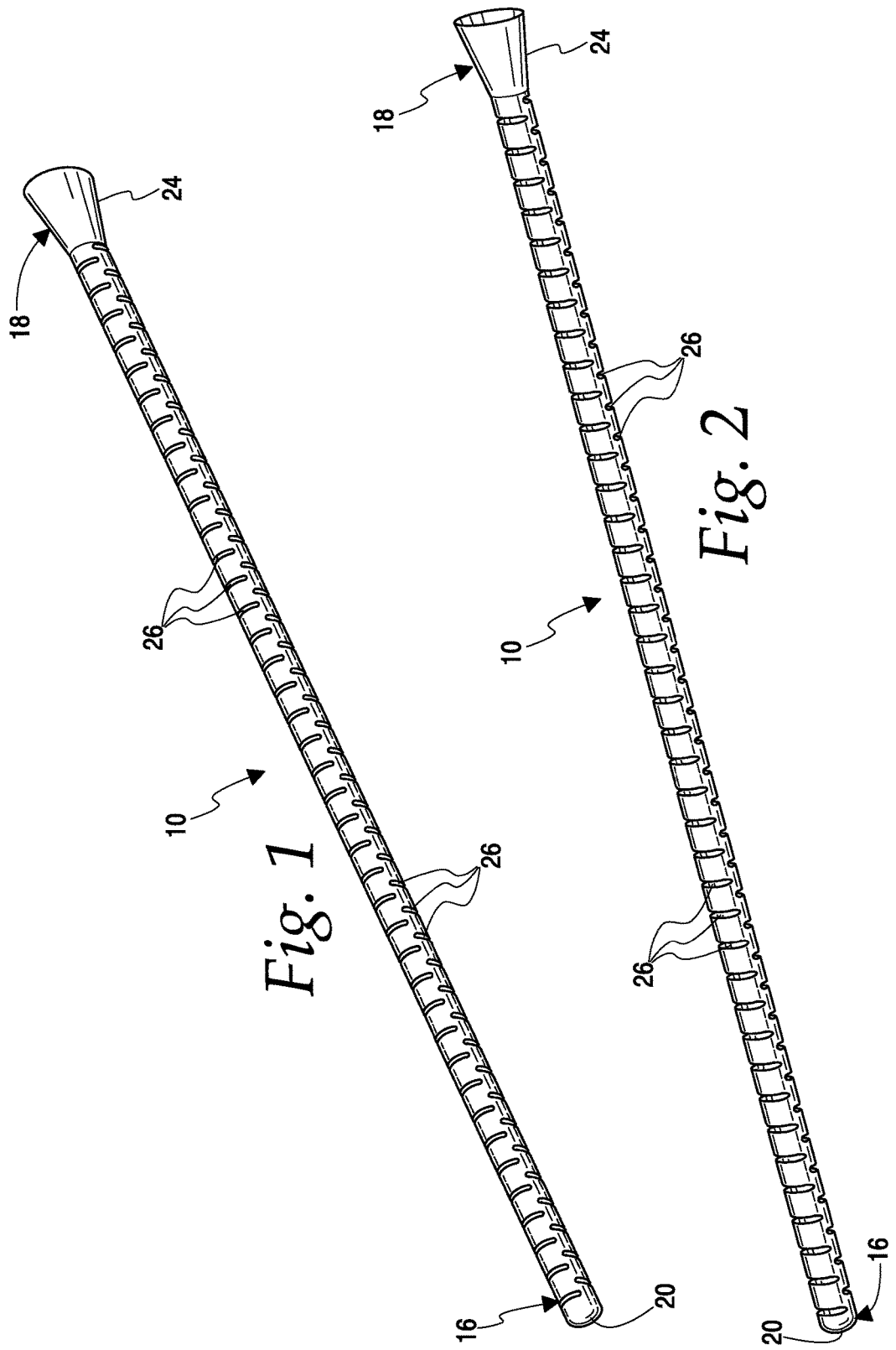

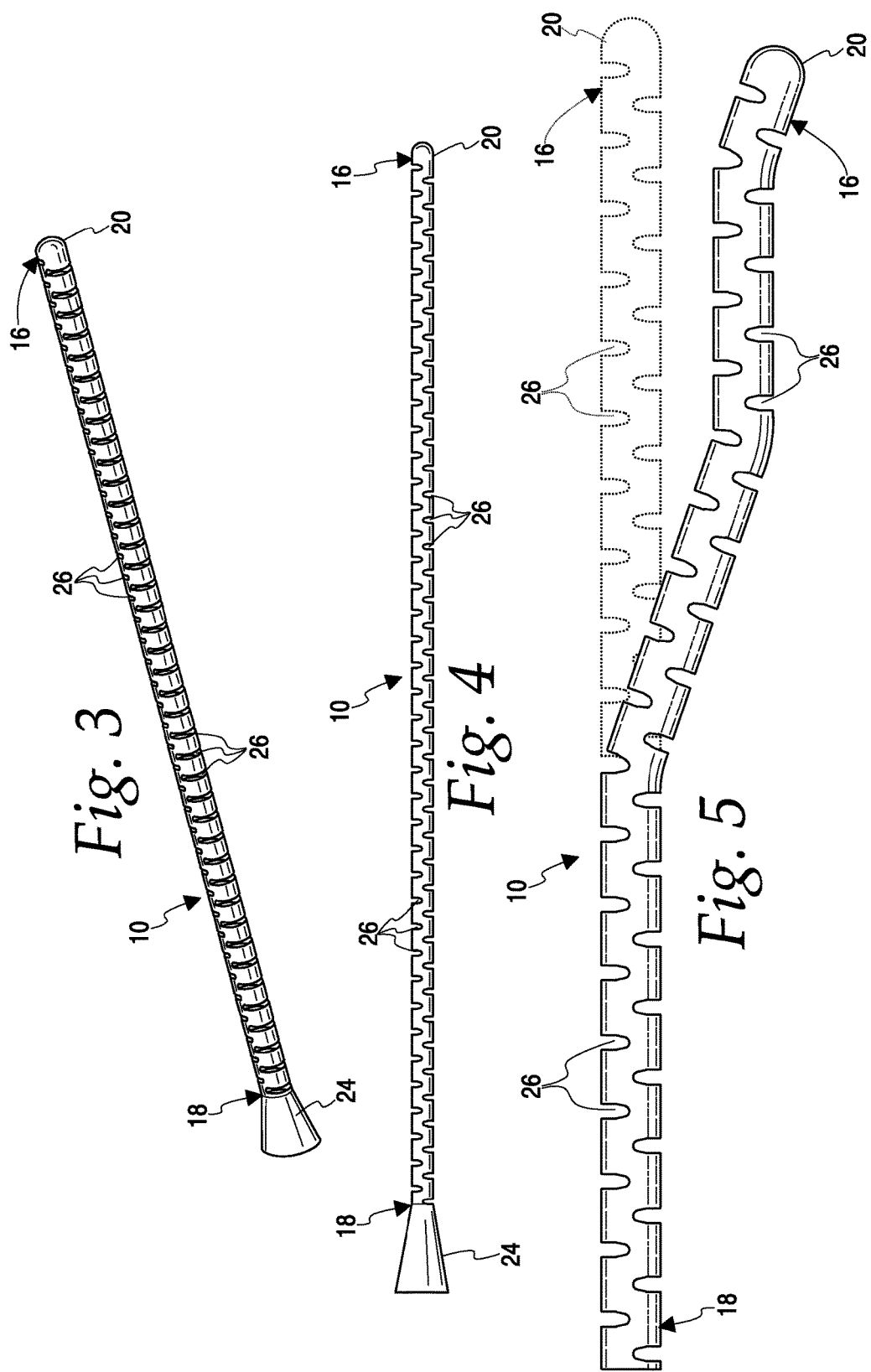

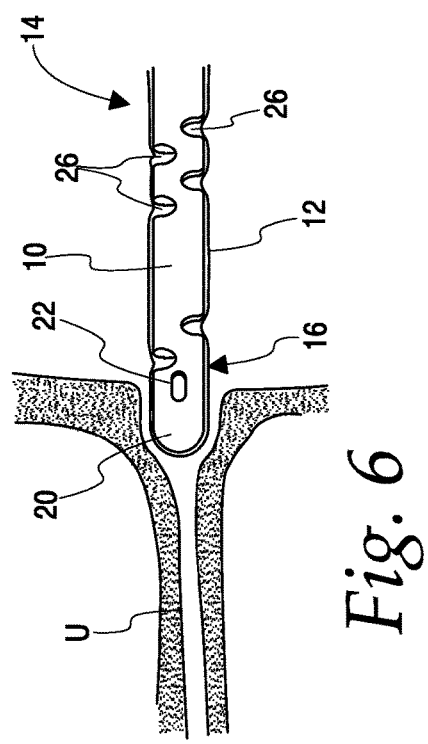
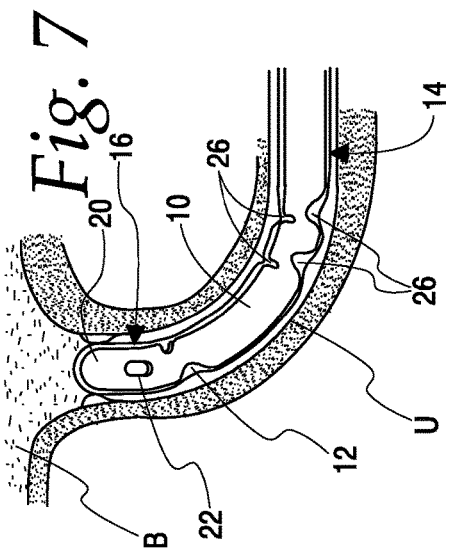
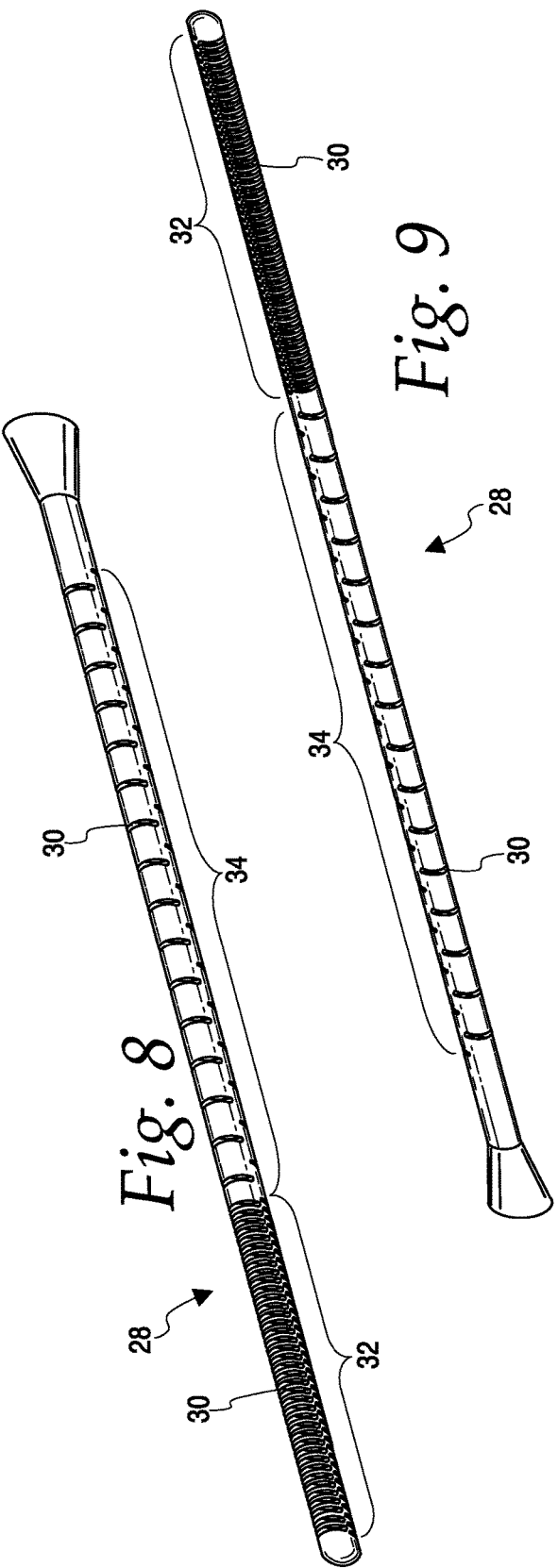

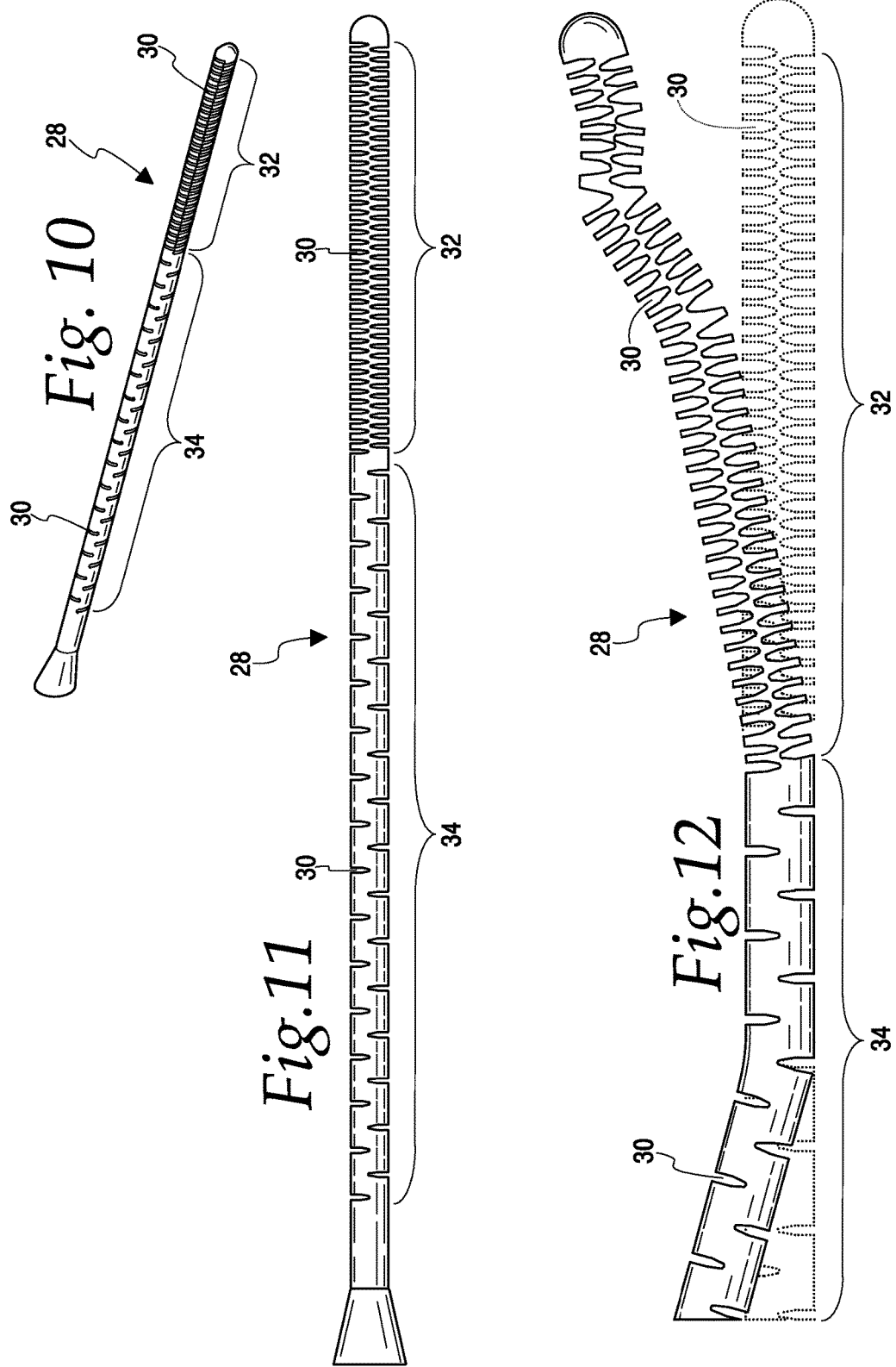

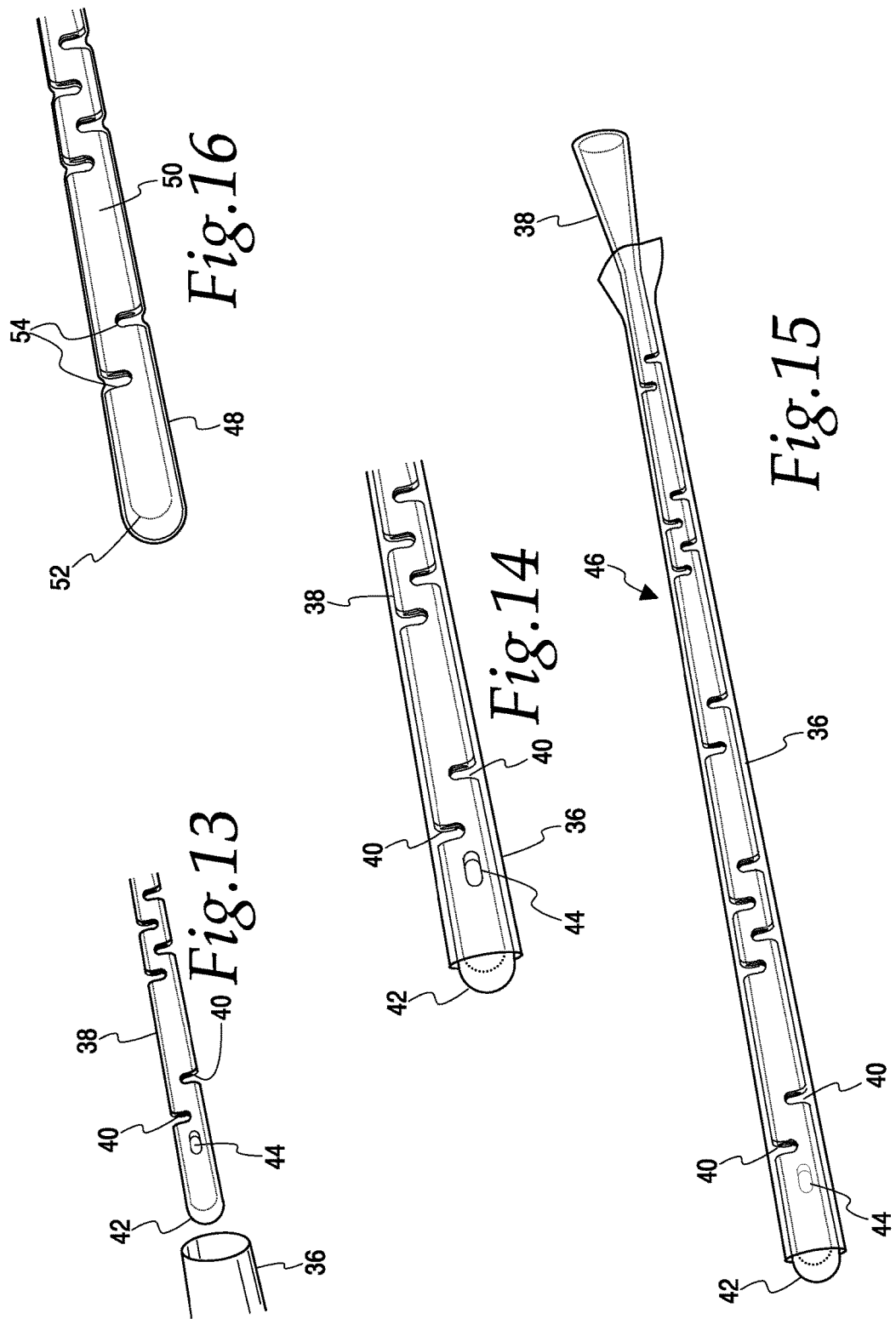

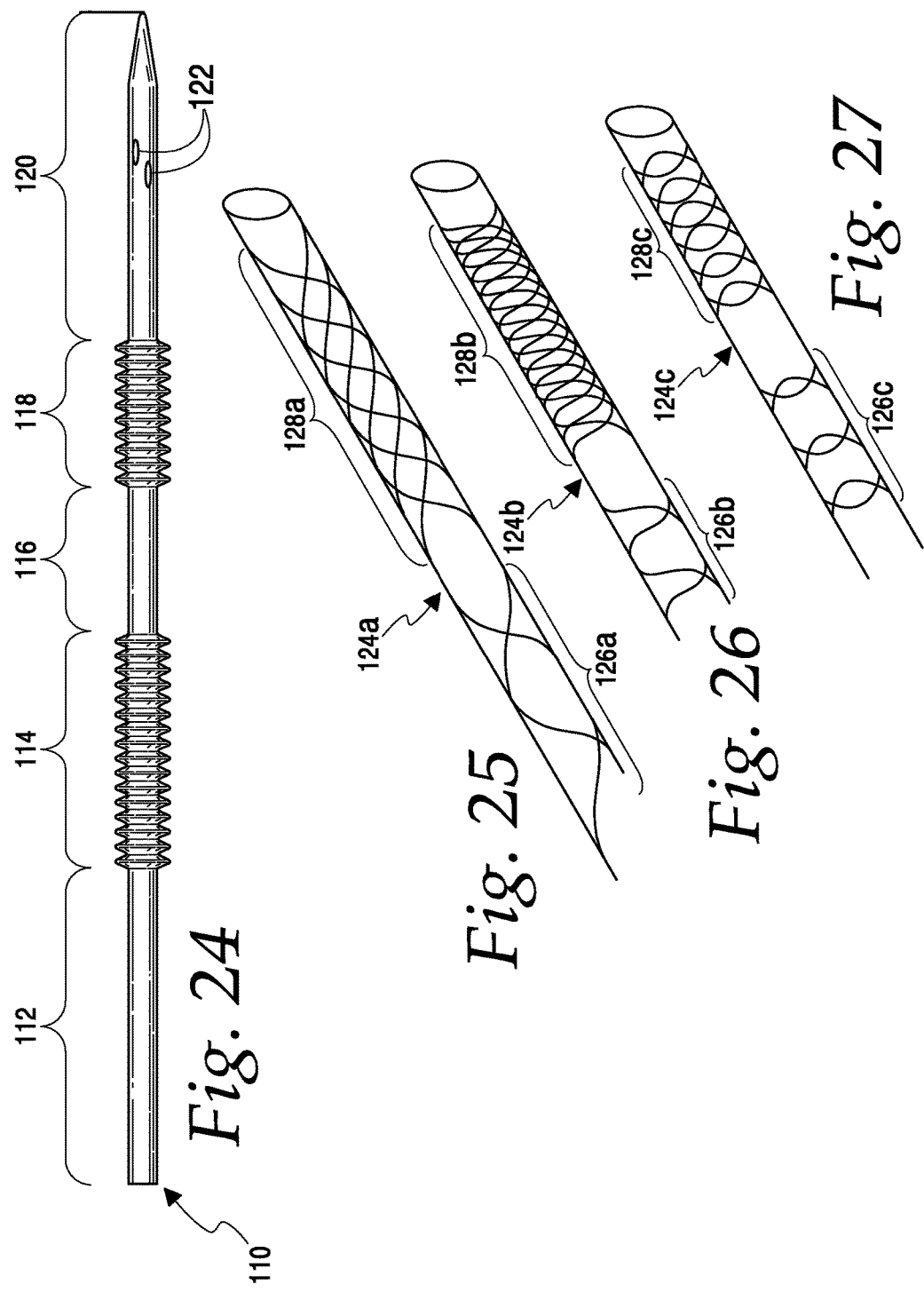

US 10,029,071 B2

URINARY CATHETERS HAVING VARYING FLEXIBILITY

RELATED APPLICATION

This application is a U.S. National Stage of PCT International Patent Application No. PCT/US13/30428, filed Mar. 12, 2013, which claims the benefit of and priority of U.S. Provisional Patent Application Ser. No. 61/726,111, filed Nov. 14, 2012, the contents of which are incorporated by reference herein.

TECHNICAL FIELD

The present disclosure generally relates to urinary catheters. More particularly, the present disclosure relates to urinary catheters having a varying flexibility along their length.

BACKGROUND

Catheters are used to treat many different types of medical conditions and typically include an elongated shaft that is inserted into and through a passageway or lumen of the body. Catheters, and in particular intermittent catheters, are commonly used by those who suffer from various abnormalities of the urinary system, such as urinary incontinence. With the advent of intermittent catheters, individuals with urinary system abnormalities can self-insert and self-remove intermittent catheters several times a day. Such catheters typically include a shaft that is sufficiently flexible to navigate the curves of the urethra (especially catheters intended for male users), yet rigid enough to be pushed through the urethra without collapsing or buckling before an end of the catheter reaches the bladder.

The present disclosure provides urinary catheters with improved flexibility/rigidity characteristics.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a male urinary catheter includes five sections. A second section is adjacent to and distal from a proximal first section. A third section is adjacent to and distal from the second section. A fourth section is adjacent to and distal from the third section. A distal fifth section is adjacent to and distal from the fourth section. The first, third, and fifth sections are relatively rigid, while the second and fourth sections are relatively flexible.

In another aspect, a method is provided for deploying a urinary catheter within a male urethra. The method includes advancing the catheter through the urethra so as to position at least portions of relatively rigid proximal first and distal fifth sections of the catheter in the bladder and penis, respectively. Second, third, and fourth sections of the catheter are positioned between the penis and the bladder, with the second and fourth sections being relatively flexible and separated by the relatively rigid third section.

In yet another aspect, a urinary catheter is provided with a catheter body and an outer layer applied to the catheter body. The body includes at least one generally planar cut defining a bending point.

In another aspect, a urinary catheter is provided with a catheter body and an outer layer applied to the catheter body. The body includes at least one corrugated section.

In yet another aspect, a urinary catheter is provided with a catheter body and an outer layer applied to the catheter body. The body includes at least one multifilament braid or weave or mesh.

In another aspect, a method is provided for manufacturing a urinary catheter. The method includes forming a catheter body by an injection molding procedure. An outer layer is extruded over at least a portion of the catheter body.

In yet another aspect, a method is provided for manufacturing a urinary catheter. The method includes forming a tube and covering at least a portion of the tube with a stencil. A cross-linking operation is performed, thereby cross-linking only a portion of the tube not covered by the stencil. This portion of the tube is cross-linked by electro-polymerization or a chemical operation.

BRIEF DESCRIPTION OF THE DRAWINGS

FIG. 1 is a perspective view of an embodiment of a urinary catheter body or scaffold according to an aspect of the present disclosure;

FIG. 2 is another perspective view of the urinary catheter body of FIG. 1;

FIG. 3 is yet another perspective view of the urinary catheter body of FIG. 1;

FIG. 4 is a side elevational view of the urinary catheter body of FIG. 1;

FIG. 5 is another side elevational view of the urinary catheter body of FIG. 1, with a proximal portion thereof shown in both a straight configuration (in broken lines) and in a bent or deflected configuration (in solid lines);

FIG. 6 illustrates the proximal end of a urinary catheter incorporating a catheter body according to the present disclosure, initially passing into a urethra;

FIG. 7 illustrates the proximal end of the urinary catheter of FIG. 6 exiting the urethra and entering into the bladder;

FIG. 8 is a perspective view of an alternative embodiment of a urinary catheter body or scaffold according to an aspect of the present disclosure;

FIG. 9 is another perspective view of the urinary catheter body of FIG. 8;

FIG. 10 is yet another perspective view of the urinary catheter body of FIG. 8;

FIG. 11 is a side elevational view of the urinary catheter body of FIG. 8;

FIG. 12 is another side elevational view of the urinary catheter body of FIG. 8, with portions thereof shown in both a straight configuration (in broken lines) and in a bent or deflected configuration (in solid lines);

FIGS. 13-15 show steps of applying a sleeve or cover or outer layer to a urinary catheter body according to an aspect of the present disclosure;

FIG. 16 shows an alternative sleeve or cover or outer layer applied to a urinary catheter body according to an aspect of the present disclosure;

FIG. 24 is a side elevational view of a catheter having corrugated sections for varying flexibility along its length;

FIG. 25 is a perspective view of a urinary catheter body or scaffold having a braided, multifilament construction;

FIG. 26 is a perspective view of another embodiment of a urinary catheter body or scaffold having a braided, multifilament construction; and FIG. 27 is a perspective view of yet another embodiment of a urinary catheter body or scaffold having a braided, multifilament construction.

DETAILED DESCRIPTION OF THE ILLUSTRATED EMBODIMENTS

Figure 17:
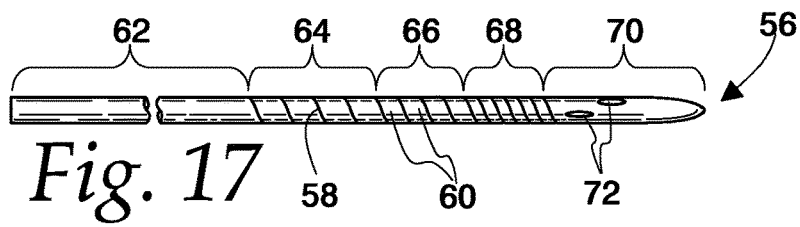
FIG. 17 is a side elevational view of another alternative embodiment of a urinary catheter body or scaffold according to an aspect of the present disclosure.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

FIGS. 1-5 show a urinary catheter body or scaffold or spine 10 onto which a sleeve or cover or outer layer 12 (described in greater detail below and shown in FIGS. 6 and 7) may be applied to form a urinary catheter 14. The urinary catheter body 10 comprises an elongated, hollow shaft or tube having a closed proximal insertion end portion 16 and an open distal end portion 18. The illustrated proximal insertion end portion 16 includes a hemispherical or otherwise atraumatic tip 20 that is suitable for insertion into and passage through a body lumen or passageway of the body, such as the urethra, for example. Unless stated to the contrary, the urinary catheter bodies and urinary catheters described herein may be adapted for either male or female use.

The proximal end insertion tip 16 may include draining holes or eyes 22 (FIGS. 6 and 7) for the drainage of bodily fluids therethrough and into an internal conduit or lumen of the urinary catheter body 10. The distal end portion 18 may include a connecting member 24, such as a funnel, for fluidly connecting the catheter 14 to a collection container, such as a collection bag into which urine drains.

The urinary catheter body 10 of FIGS. 1-5 includes a plurality of cuts or slits 26 along its length that define bending points or bending features. The cuts or slits 26 may be formed by any of a number of methods, including being formed either during the formation of the body 10 itself (e.g., by a molding process) or being added after the body 10 has been formed (e.g., by a cutting process). In a preferred embodiment, the body 10 is an injection-molded piece, with the mold including elements configured to define the various cuts or slits 26 during the molding process.

In the illustrated embodiment, each cut or slit 26 comprises the absence of material in a plane generally perpendicular to a central axis of the body 10. In other embodiments, one or more of the cuts or slits 26 may be oriented at a non-perpendicular angle with respect to the axis of the body 10 and/or be substantially non-planar. The size (e.g., the degree to which they extend toward the axis of the body 10 and/or their extent along the axis of the body 10 and/or their angular extent along the perimeter of the body 10) and configuration of each cut or slit 26 may vary, but in the illustrated embodiment, each cut or slit 26 extends approximately half way through the body 10. In one embodiment, the cuts or slits 26 may extend entirely through the wall of the body 10 to communicate with the internal lumen thereof. In other embodiments, the cuts or slits 26 may be more shallow, defining grooves that extend only partially through the thickness of the wall of the body 10, rather than passing entirely through the wall.

As best shown in FIGS. 4 and 5, the body 10 may comprise a plurality of alternating cuts or slits 26, with each cut or slit being oriented approximately 180° away from the adjacent cuts or slits. In other words, the cuts or slits 26 alternate between positions on one side of the body 10 (the upper side of the body 10 in the orientation of FIGS. 4 and 5) and the opposite side of the body 10 (the lower side of the body 10 in the orientation of FIGS. 4 and 5). In other embodiments, adjacent cuts or slits are not necessarily spaced 180° away from each other, but may be positioned at some other angle with respect to each other (e.g., by being 45° or 90° apart about the perimeter of the body). It is also within the scope of the present disclosure for the adjacent cuts or slits to be positioned at the same angular position (i.e., spaced 0° away from each other about the perimeter of the urinary catheter body). Furthermore, FIGS. 1-5 show the several cuts or slits 26 being approximately equally spaced along the length of the body 10, but it is also within the scope of the present disclosure for the cuts or slits 26 to be non-uniformly spaced along the length of the body 10.

FIGS. 6 and 7 show the proximal end portion 16 of a urinary catheter 14 incorporating a catheter body 10 having a plurality of cuts or slits 26. The catheter 14 is sufficiently rigid to be pushed into (FIG. 6) and through a urethra U without collapsing or buckling. The cuts or slits 26 impart to the catheter 14 sufficient flexibility to follow the curvature of the urethra U (which is particularly important for male users) until the proximal end portion 16 enters the bladder B (FIG. 7). For example, as the catheter 14 is advanced further into the urethra U and bends upwardly (in the orientation of FIG. 7), the cuts or slits 26 on the upper surface of the catheter body 10 tend to close (or move toward a more closed position) and the cuts or slits 26 on the lower surface of the catheter body 10 tend to open (or move toward a more open position). When the proximal end portion 16 has been positioned within the bladder B, urine may enter the hollow interior of the catheter 14 via a pair of holes or eyes 22 (only one of which is visible in FIGS. 6 and 7) and flow through the body 10 until it exits the connecting member at the distal end portion.

The flexibility/rigidity characteristics of a catheter 14 formed using a body 10 having a plurality of cuts or slits 26 depends upon the configuration and orientation of the various cuts or slits 26. Thus, it should be understood that the embodiment of FIGS. 1-5 is merely exemplary of one possible configuration of a suitable body, rather than being limiting. In the illustrated embodiment of FIGS. 1-5, the catheter body 10 has different flexibilities in different bending planes. For example, the catheter body 10 will be generally flexible when bent or deformed in the direction of the cuts or slits 26 (i.e., in a vertical direction when in the orientation of FIGS. 4 and 5), but more rigid in a perpendicular direction (i.e., into or out of the page when in the orientation of FIGS. 4 and 5). In general, the tendency of the cuts or slits 26 to close/open when bent in a particular direction renders the catheter body 10 flexible in that direction. On the other hand, it will be more difficult to bend the catheter body 10 in a direction that does not tend to close or open the cuts or slits 26 (i.e., into and out of the page when in the orientation of FIGS. 4 and 5), rendering the catheter body 10 more rigid in that direction. In other embodiments, the cuts or slits may be configured and oriented so as to impart to the catheter body flexibility in only one bending direction or the same approximate flexibility in all bending directions.

FIGS. 8-12 show a urinary catheter body or scaffold or spine 28 having a different cut/slit configuration than the catheter body 10 of FIGS. 1-5. By providing the catheter body 28 with a different cut/slit configuration, it has a different flexibility/rigidity profile than the catheter body 10 of FIGS. 1-5. In particular, the catheter body 28 illustrated in FIGS. 8-12 has a plurality of identical, alternating cuts or slits 30, as in the embodiment of FIGS. 1-5, but has at least two sections 32 and 34 in which adjacent cuts or slits 30 are spaced different distances apart. In a more proximal section 32, there is a relatively large number of cuts/slits 30, and adjacent cuts or slits 30 are relatively close together. In contrast, there are fewer cuts/slits 30 which are relatively far apart in a more distal section 34.

Similar to the embodiment of FIGS. 1-5, the catheter body 28 of FIGS. 8-12 is relatively flexible in a bending direction directly toward or away from the cuts/slits 30 (i.e., in a vertical direction when in the orientation of FIGS. 11 and 12, which tends to open/close the cuts/slits 30), while being more rigid in the perpendicular bending direction (i.e., into or out of the page when in the orientation of FIGS. 11 and 12, because bending the catheter body 28 in that direction neither opens nor closes the cuts/slits 30). However, by including more cuts or slits 30 and spacing them closer together, the more proximal section 32 of the catheter body 28 of FIGS. 8-12 is more flexible in a bending direction directly toward or away from the cuts/slits 30 than the catheter body 10 of FIGS. 1-5 and the more distal section 34 of FIGS. 8-12. As for the more distal section 34, it is more rigid than the catheter body 10 of FIGS. 1-5 and the more proximal section 32 of FIGS. 8-12 in that same bending direction, due to having fewer cuts/slits 30 that are spaced farther apart. Such a configuration may be advantageous, in that the more proximal section 32 (which is advanced into or adjacent to the bladder) is relatively flexible, to allow it to traverse the curvature of the urethra (particularly the male urethra), while the more distal section 34 (which is advanced only partly through the urethra) is more rigid, which allows the catheter 30 to be moved through the urethra without collapsing or buckling. It will be appreciated that such a configuration allows the catheter to perform like a dual-durometer catheter without the need for employing different materials or durometer-modification techniques.

While the embodiment of FIGS. 8-12 is illustrated with two relatively discrete sections 32 and 34, it is within the scope of the present disclosure for the catheter body to have more than two sections with different flexibility/rigidity sections. For example, the catheter body 28 of FIGS. 8-12 may be provided with an intermediate section between the other two sections 32 and 34, with the intermediate section having a greater flexibility than the more distal section 34 and a lesser flexibility than the more proximal section 32. In another example, the catheter body may include alternating flexible and rigid sections, which may be particularly beneficial for male urinary catheters, as will be described in greater detail below.

As previously described, the cuts or slits may pass entirely through the tube wall, thereby defining a fluid pathway between the central lumen or hollow interior of the body and the region surrounding the catheter body. For this reason, at least a portion of the body may be covered by a sleeve or cover or outer layer to prevent urine from flowing through the cuts or slits. On the other hand, it may be advantageous for the most proximal cuts or slits to remain uncovered and act as holes or eyes to drain urine from the bladder into the catheter. Even if the cuts or slits do not pass entirely through the tube wall, a sleeve or cover or outer layer may be provided over the catheter body to provide a smooth outer surface for contacting the wall of the urethra.

If provided, the sleeve or cover or outer layer may be variously configured and applied using any of a number of suitable methods. For example, FIGS. 13-15 show a sleeve or cover or outer layer 36 comprising a heat-shrinkable material being provided (FIG. 13) and positioned about at least a portion of the catheter body 38 (FIG. 14). With the outer layer 36 in place, heat is applied to shrink the outer layer 36 and secure it to the catheter body 38 (FIG. 15). In the embodiment of FIGS. 13-15, the outer layer 36 overlays the most proximal cuts/slits 40 and at least a portion of the proximal end insertion tip 42. After the outer layer 36 has been applied, an additional step (e.g., a cutting or punching step) may be carried out to form eyes 44 in the proximal end insertion tip 42 and corresponding openings through the outer layer 36 (FIG. 15) or to form openings in the portion of the outer layer 36 overlaying selected cuts/slits 40 (e.g., the most proximal cuts/slits 40) to define drainage openings into the catheter 46. It is also within the scope of the present disclosure for the eyes 44 to be formed prior to application of the outer layer 36, with openings through the outer layer 36 subsequently formed to provide access to the eyes 44.

FIG. 16 shows an alternative sleeve or cover or outer layer 48, which is applied to a catheter body 50 using an extrusion process. If the outer layer 48 is extruded so as to cover all or a portion of the proximal insertion end portion 52 of the body 50, including the cuts/slits 54, an additional step (e.g., a cutting or punching step) may be carried out to form openings in the portion of the outer layer 48 overlaying selected cuts/slits 54 (as shown in FIG. 16) or to form eyes and corresponding openings through the outer layer 48.

Regardless of how the sleeve or cover or outer layer is applied to the catheter body, it may be preferred for it to be hydrophilic or have hydrophilic properties such that, when wetted or hydrated, it becomes lubricious for ease of passage through the urethra. In other embodiments, the sleeve or cover or outer layer may be formed of a material that is compatible with lubricants, thereby allowing a lubricant to be applied to the catheter to provide a lubricious surface. As will be described in greater detail herein, the sleeve or cover or outer layer may be configured to contribute to the varying flexibility of the urinary catheter along its length.

Figure 18:
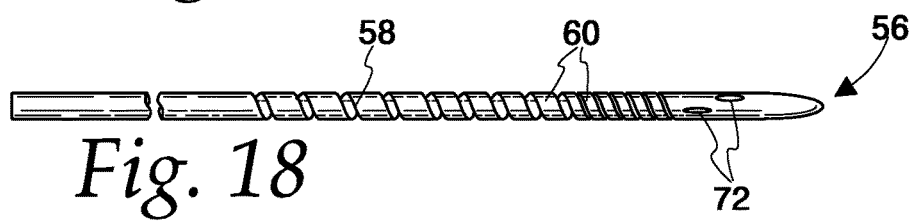
FIG. 18 is a side elevational view of the urinary catheter body of FIG. 17, in a stretched or elongated configuration.

In addition to the use of a plurality of cuts or slits, there are other ways of imparting varying flexibility to a urinary catheter body or scaffold or spine. For example, FIGS. 17 and 18 show a urinary catheter body 56 comprising a hollow tube (formed by injection molding or extrusion or any other suitable method) with a helical or spiral cut or slit 58 through its tubular wall that effectively defines a coiled ribbon having a plurality of turns 60. FIG. 18 shows how the spiral cut 58 allows the catheter body 56 to be elongated, but it will be appreciated that the spiral cut 58 also imparts flexibility to the catheter body 56 to allow it to traverse a urethra.

As shown in FIGS. 17 and 18, the pitch of the spiral cut 58 may vary along the length of the catheter body 56, thereby imparting a varying flexibility to the catheter body 56. FIG. 17 shows the catheter body 56 divided into five sections, each having a different flexibility than the adjacent section(s). A first distal end section 62, which may include a funnel or connecting member (not illustrated), omits a spiral cut, rendering it substantially rigid. A second section 64, positioned adjacent to and proximally of the distal end section 62, includes the spiral cut 58. The spiral cut 58 renders the second section 64 more flexible than the distal end section 62, but has a relatively large pitch to impart the second section 64 with a degree of rigidity. Preferably, the second section 64 is sufficiently flexible to traverse a portion of the urethra, but sufficiently rigid to be pushed through the urethra without collapsing or buckling.

Proximal of the second section 64 are a third section 66 and a fourth section 68, with the third section 66 being positioned between the second and fourth sections 64 and 68. The same spiral cut 58 from the second section 64 of the catheter body 56 continues in the third and fourth sections 66 and 68, but has a smaller pitch in the third and fourth sections 66 and 68. In the illustrated embodiment, the pitch of the spiral cut 58 is smaller in the third section 66 than in the second section 64, and smaller in the fourth section 68 than in the third section 66. A smaller pitch results in a greater flexibility, meaning that the urinary catheter body 56 is more flexible in the third section 66 than in the second section 64, and most flexible in the fourth section 68. Beyond the fourth section 68 is a fifth or proximal end section 70, which may include a pair of holes or eyes 72 but omits the spiral cut 58, rendering it substantially rigid, similar to the distal end section 62. While FIG. 17 shows the catheter body 56 as having a single, continuous spiral cut 58, it is within the scope of the present disclosure for the catheter body 56 to instead include a plurality of spiral cuts, such as discrete spiral cuts for each of the second, third, and fourth sections 64, 66, and 68.

As in the embodiments discussed previously, an outer layer or sleeve or cover may be applied to the urinary catheter body 56 of FIGS. 17 and 18 using any of a number of suitable of methods (including heat-shrinking or extrusion). If an outer layer is provided, it may be advantageous to treat or configure the turns 60 of the spiral cut catheter body 56 to prevent cutting or pinching the outer layer when the catheter is flexed away from a straight configuration. According to one method, one or more of the turns 60 may be provided with a chamfered or beveled or rounded edge 74 (FIG. 19) to decrease the risk of adjacent edges damaging the outer layer if the adjacent edges contact each other during use. It may be preferred for both edges defined by the spiral cut 58 to be chamfered or beveled or rounded along the entire length of the spiral cut 58 to decrease the risk of the edges of the turns 60 damaging the outer layer during use.

Figure 19:
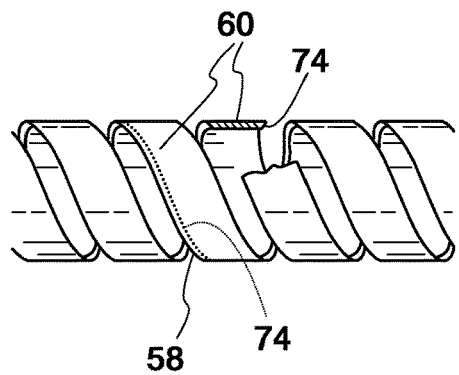
FIG. 19 is a detail view of a portion of the urinary catheter body of FIG. 17.
Figure 20:
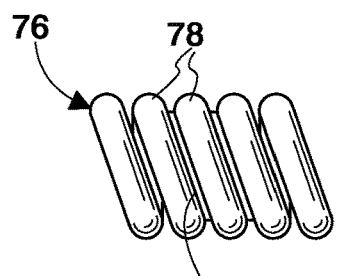
FIG. 20 illustrates a coil configuration that may be incorporated into a urinary catheter body of the type shown in FIG. 17.

FIG. 20 illustrates a variation of the catheter body design of FIGS. 17-19. In the embodiment of FIG. 20, rather than employing a spiral cut, at least a portion of the catheter body is defined by a coiled filament 76 having a plurality of loops or turns or coils 78. As in the embodiment of FIGS. 17-19, the loops 78 may be provided with a varying pitch to vary the flexibility of the catheter body along its length. Similar to the embodiment of FIGS. 17-19, a catheter body may be provided with only selected portions defined by a coiled filament 76, with other sections defined by a relatively rigid, uncut, uncoiled tubular portion. Alternatively, sections including a coiled filament 76 may be made more rigid by providing joinder means 80 to seal or join adjacent loops 78 together and prevent them from separating from each other. The joinder means 80 may be variously provided, such as being provided as a clip or an adhesive or a weld or any other suitable means for preventing loop separation and limiting flexibility. According to one method, a filament is wrapped around a mandrel to define a coil shape, with the mandrel then being heated to seal selected coils together.

Figure 21:
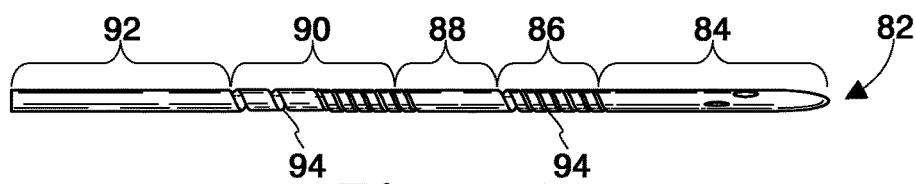
FIG. 21 illustrates a preferred configuration of a urinary catheter body of the type shown in FIG. 17, configured for use in a male urethra.
Figure 22:
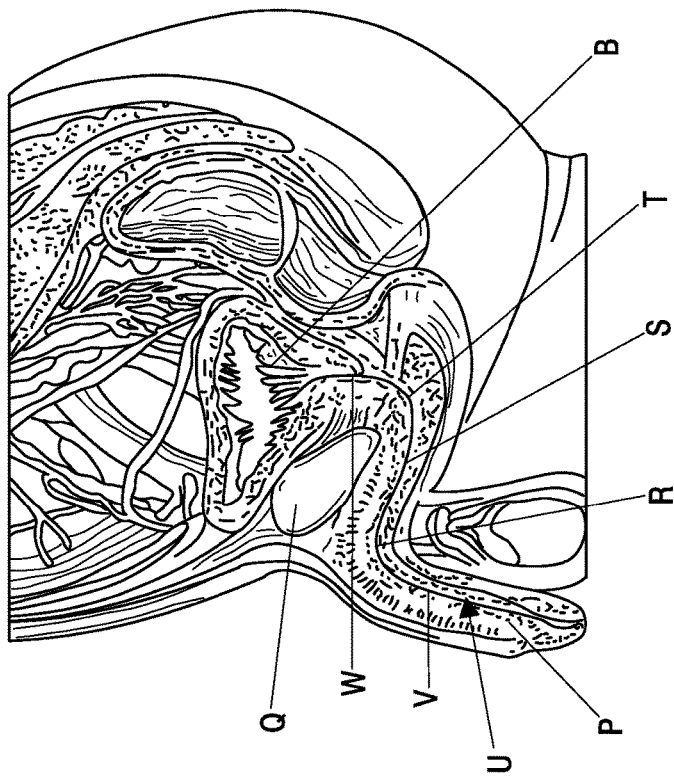
FIG. 22 illustrates a male urinary system in which a urinary catheter employing the urinary catheter body of FIG. 21 may be deployed.

The flexibility profile of the urinary catheter body 56 of FIGS. 17 and 18 is merely exemplary, and it should be understood that other flexibility profiles may be practiced without departing from the scope of the present disclosure. For example, FIG. 21 shows a urinary catheter body 82 having a flexibility profile that is especially well-suited for use in a male urethra U (FIG. 22). As shown in FIG. 22, the male urethra U defines a tortuous pathway, with a relatively sharp turn in the transition region R between the penis P and the portion S of the urethra U beneath the prostate Q. The urethra U defines another relatively sharp turn in the transition region T between the portion S beneath the prostate Q and the bladder B. Besides these two transition regions, the other portions of the urethra U are relatively straight or linear (i.e., the portion V of the urethra U defined by the penis P, the portion S of the urethra U beneath the prostrate Q, and the portion W immediately outside of the bladder B).

The catheter body 82 of FIG. 21 is provided with five sections that correspond generally to the aforementioned transition regions and portions of the urethra U. In particular, the illustrated catheter body 82 includes a proximal first section 84, a second section 86 adjacent to and distal of the first section 84, a third section 88 adjacent to and distal of the second section 86, a fourth section 90 adjacent to and distal of the third section 88, and a distal fifth section 92 adjacent to and distal of the fourth section 90. The sections alternate between relatively rigid sections (the first, third, and fifth sections 84, 88, and 92) and relatively flexible sections (the second and fourth sections 86 and 90). While FIG. 21 shows the catheter body 82 as having spiral cuts 94 in the relatively flexible second and fourth sections 86 and 90, it should be understood that any other methods of imparting varying flexibility to a section of a catheter or a catheter body may alternatively be employed. Preferably, one of the methods described herein (e.g., the cuts or slits of FIGS. 1-16 or the coils of FIG. 20) is used to provide the illustrated flexibility profile.

When a urinary catheter incorporating the alternating flexibility profile of FIG. 21 is properly positioned within the urethra U, the relatively rigid sections are configured to be positioned in the less curved or the generally straight or linear portions of the urethra U. In particular, the relatively rigid proximal first section 84 of the catheter or catheter body 82 is configured to be at least partially positioned within the bladder B and the portion W of the urethra U leading into the bladder B when the catheter has been properly inserted. The relatively rigid third section 88 of the catheter or catheter body 82 is configured to be at least partially positioned within the portion S of the urethra U that is beneath the prostate Q when the catheter has been properly inserted. The relatively rigid distal fifth section 92 of the catheter or catheter body 82 is configured to be at least partially positioned within the portion V of the urethra U defined by the penis P.

In the illustrated embodiment, the relatively rigid sections are illustrated as being substantially free of any flexibility-enhancing feature (e.g., a spiral cut), but it is within the scope of the present disclosure to provide one or more of the relatively rigid sections with flexibility-enhancing features. However, it may be preferred for the relatively rigid sections to be less flexible than the relatively flexible sections 86 and 90 even when they include flexibility-enhancing features to ensure that the catheter has sufficient column strength to be maneuvered through the urethra U without collapsing or buckling.

When a urinary catheter incorporating the alternating flexibility profile of FIG. 21 is properly positioned within the urethra U, the relatively flexible sections 86 and 90 are configured to be positioned in the more curved portions of the urethra U. In particular, the relatively flexible second section 86 of the catheter or catheter body 82 is configured to be at least partially positioned in the transition region T between the between the portion S of the urethra U beneath the prostate Q and portion W leading into the bladder B when the catheter has been properly inserted. It may be advantageous for the second section 86 to extend partially into one or both of these portions S and W of the urethra U to ensure that the catheter successfully traverses the curved transition region T. The relatively flexible fourth section 90 of the catheter or catheter body 82 is configured to be at least partially positioned in the transition region R between the portion V of the urethra U defined by the penis P and the portion S of the urethra U beneath the prostate Q when the catheter has been properly inserted. It may be advantageous for the fourth section 90 to extend partially into one or both of these portions S and V of the urethra U to ensure that the catheter successfully traverses the curved transition region R.

Either of the relatively flexible sections 86 and 90 of the catheter or catheter body 82 may have a substantially uniform flexibility (as in the second section 86 of FIG. 21) or a varying flexibility (as in the fourth section 90 of FIG. 21). Furthermore, the lengths of the relatively flexible sections (as well as the relatively rigid sections) of the catheter or catheter body may vary, and it should be understood that the lengths of the sections illustrated in FIG. 21 are not necessarily to scale.

While various techniques are separately described for imparting varying flexibility along the length of a urinary catheter or catheter body, it is also within the scope of the present disclosure for the various techniques to be combined in a single catheter or catheter body. For example, one portion of a catheter body may include a plurality of cuts or slits of the type described above in reference to the embodiments of FIGS. 1-16, while another portion of the same catheter body may include a spiral cut of the type described above in reference to the embodiments of FIGS. 17 and 18.

Figure 23:
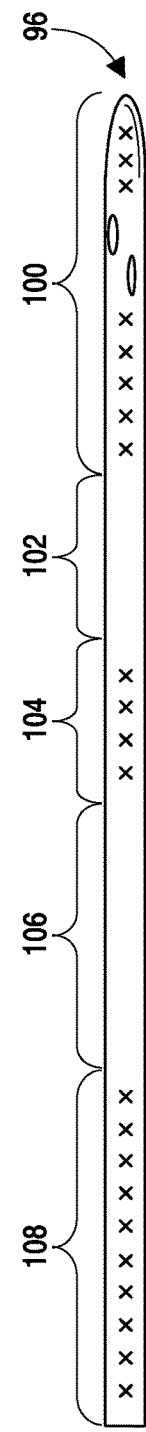
FIG. 23 is a side elevational view of a catheter having selectively cross-linked sections for varying flexibility along its length.

According to another aspect of the present disclosure, which may be used alone or in combination with the methods and apparatus described previously, the outer layer or sleeve or cover or tube may be configured to impart a varying flexibility to the urinary catheter. In one specific example, at least a portion of the outer layer or tube may be cross-linkable, such that cross linking may be carried out in one portion of the outer layer and not in another (or to a lesser extent in another area), such that the cross-linked portion is more rigid than the other portion. If used in combination with catheter bodies of the type described herein, a partially cross-linked outer layer or tube may supplement the rigidity/flexibility of the catheter in selected locations. For example, FIG. 23 shows a completed catheter 96 comprising an outer layer or tube 98 applied to a catheter body of the type shown in FIG. 21. The outer layer or tube 98 may comprise five sections 100, 102, 104, 106, and 108, with each section corresponding to one of the sections of the underlying catheter body. In this case, the sections 100, 104, and 108 of the outer layer or tube 98 correspond to the first, third, and fifth sections 84, 88, and 92 of the catheter body 82 (respectively), and may be provided with cross-links to further increase the rigidity of those sections. The sections 102 and 106 of the outer layer or tube 98 correspond to the second and fourth sections 86 and 90 of the catheter body 82 (respectively), and may be substantially free of cross-linking (or at least be cross-linked to a lesser extent than the sections 100, 104, and 108 of the outer layer or tube 98 corresponding to the first, third, and fifth sections 84, 88, and 92 of the catheter body 82) to retain the flexibility of those sections. The same pattern (i.e., alternating cross-linked and non- or lesser-cross-linked sections) may alternatively be employed with other catheter bodies or inner layers (e.g., ones having a relatively uniform flexibility along their length) to create a urinary catheter having a relatively rigid proximal first section, a relatively flexible second section adjacent to and distal of the first section, a relatively rigid third section adjacent to and distal of the second section, a relatively flexible fourth section adjacent to and distal of the third section, and a relatively rigid distal fifth section adjacent to and distal of the fourth section. Other flexibility profiles (e.g., profiles in which flexibility increases from one end of the catheter to the other) may also be imparted to catheters by outer layers or tubes according to this aspect of the present disclosure.

Various methods may be employed to impart different amounts of cross-links to the different sections of the outer layer or tube. For example, the outer layer or tube may be made of a relatively homogeneous, cross-linkable polymer material. In one embodiment, the cross-linkable polymer material may comprise a mixture of one or more of the following materials: polyamides, polyvinyl alcohol, polyvinyl chloride, poly(ε-caprolactone) with polymethylvinylsiloxane, poly(ethylene-co-(vinylacetate)) with dicumylperoxide, poly(L-lactide) and poly(glycolide-co-(ε-caprolactone))-segments, multiblock copolyesters from poly (ε-caprolactone) and PEG and chain extender based on cinnamic acid groups, poly(ε-caprolactone) dimethacrylate and n-butyl acrylate, oligo(ε-caprolactone) diols, oligo (p-dioxanone) diols and diisocyanate, linear density polyethylene, linear low density polyethylene and high density polyethylene. In other embodiments, other cross-linkable materials may be used to form the outer layer or tube.

After the catheter has been formed, a stencil or mask could be applied over the catheter to overlay selected sections of the outer layer or tube. With the stencil or mask in place, a cross-linking step or operation (e.g., electropolymerization or exposure to ultraviolet light or radiation or a chemical cross-linking operation) may be carried out, with the stencil or mask being positioned between a cross-linking agent and the aforementioned selected sections of the outer layer or tube. In the uncovered sections, the cross-linking agent interacts with the material of the outer layer or tube to cross-link the material. In the covered sections, the cross-linking agent is prevented from interacting with the material of the outer layer or tube, thereby preventing cross-linking of the material in the sections of the outer layer or tube that are covered by the stencil or mask. The stencil or mask may be moved along the length of the outer layer or tube or be removed during the cross-linking operation to further vary the extent of cross-linking along the length of the catheter.

As noted, the outer layers or tubes and cross-linking techniques described herein may be used with catheter bodies according to the present disclosure or may be practiced separately. For example, a selectively cross-linked outer layer or tube may be used in combination with an extruded inner layer or member or an inner layer or member that is formed using a method other than molding. In another example, a tube having cross-linking in selected regions may be provided on its own to comprise a catheter body, with no additional inner layer or scaffold.

FIG. 24 illustrates an example of another urinary catheter body 110 having a varying flexibility along its length, according to an aspect of the present disclosure. The urinary catheter body 110 comprises a hollow tube (formed by injection molding or extrusion or any other suitable method) with at least one corrugated section and at least one non-corrugated section. In comparison to the non-corrugated section, the corrugated section is relatively flexible, thereby imparting a varying flexibility along the length of the catheter body.

In the illustrated embodiment, the urinary catheter body 110 has three non-corrugated sections 112, 116, and 120 and two corrugated sections 114 and 118, with each corrugated section positioned between two of the non-corrugated sections. A first distal end section 112, which may include a funnel or connecting member (not illustrated), has a generally uniform outer diameter or is otherwise non-corrugated, rendering it more rigid than the corrugated sections. A second section 114, positioned adjacent to and proximally of the distal end section 112, is corrugated, with a varying outer diameter that renders the second section 114 more flexible than the distal end section 112. Preferably, the second section 114 is sufficiently flexible to traverse a portion of the urethra, but sufficiently rigid to be pushed through the urethra without collapsing or buckling.

Proximal of the second section 114 are a third section 116 and a fourth section 118, with the third section 116 being positioned between the second and fourth sections 114 and 118. The same or a different corrugation profile from the second section 114 of the catheter body 110 is provided in the fourth section 118, with the third section 116 being non-corrugated, rendering it more rigid than the second and fourth sections 114 and 118 to which it is adjacent. If the second and fourth sections 114 and 118 having the same corrugation profiles, they will have substantially similar flexibilities, whereas they will have different flexibilities if their corrugation profiles are different. Beyond the fourth section 118 is a fifth or proximal end section 120, which may include a pair of holes or eyes 122 but is non-corrugated, rendering it more rigid than the corrugated sections, similar to the distal end section 112 and the third section 116.

When a urinary catheter incorporating the alternating flexibility profile of FIG. 24 is properly positioned within the urethra U (FIG. 22), the relatively rigid sections are configured to be positioned in the less curved or the generally straight or linear portions of the urethra U. In particular, the relatively rigid proximal section 120 of the catheter or catheter body 110 is configured to be at least partially positioned within the bladder B and the portion W of the urethra U leading into the bladder B when the catheter has been properly inserted. The relatively rigid third section 116 of the catheter or catheter body 110 is configured to be at least partially positioned within the portion S of the urethra U that is beneath the prostate Q when the catheter has been properly inserted. The relatively rigid distal first section 112 of the catheter or catheter body 110 is configured to be at least partially positioned within the portion V of the urethra U defined by the penis P.

When a urinary catheter incorporating the alternating flexibility profile of FIG. 24 is properly positioned within the urethra U, the relatively flexible sections 114 and 118 are configured to be positioned in the more curved portions of the urethra U. In particular, the relatively flexible fourth section 118 of the catheter or catheter body 110 is configured to be at least partially positioned in the transition region T between the between the portion S of the urethra U beneath the prostate Q and portion W leading into the bladder B when the catheter has been properly inserted. It may be advantageous for the fourth section 118 to extend partially into one or both of these portions S and W of the urethra U to ensure that the catheter successfully traverses the curved transition region T. The relatively flexible second section 114 of the catheter or catheter body 110 is configured to be at least partially positioned in the transition region R between the portion V of the urethra U defined by the penis P and the portion S of the urethra U beneath the prostate Q when the catheter has been properly inserted. It may be advantageous for the second section 114 to extend partially into one or both of these portions S and V of the urethra U to ensure that the catheter successfully traverses the curved transition region R.

While the illustrated embodiment of the urinary catheter body 110 may be preferred, different configurations of the urinary catheter body 110 (e.g., having different numbers of corrugated and non-corrugated sections or having sections with different lengths than those illustrated in FIG. 24) may also be employed without departing from the scope of the present disclosure. In one variation, an individual corrugated section has a varying corrugation profile, thereby imparting a varying flexibility to that section. In yet another variation, the entirety of the urinary catheter body is corrugated, with a varying corrugation profile to impart a varying flexibility along the length of the urinary catheter body.

As in the embodiments discussed previously, an outer layer or sleeve or cover may be applied to the urinary catheter body 110 of FIG. 24 using any of a number of suitable of methods (including heat-shrinking or extrusion). While the outer diameter of the urinary catheter body 110 varies in the corrugated sections, with at least a portion of the corrugated sections having a different outer diameter than the outer diameter of the non-corrugated sections, it may be preferred for the outer layer or sleeve or cover to have a uniform outer diameter when applied.

According to another aspect of the present disclosure, a urinary catheter body may be defined by a multifilament braid or weave or mesh to impart to it a varying flexibility along its length. The braid or weave or mesh may be formed according to any suitable method. FIGS. 25-27 illustrate three embodiments of urinary catheter bodies 124a, 124b, and 124c defined by a multifilament braid or weave or mesh. In each embodiment, the urinary catheter body 124a, 124b, 124c has a first section 126a, 126b, 126c and a second section 128a, 128b, 128c, respectively. In each embodiment, the first and second sections are defined by a braid or weave or mesh, with the pattern density (e.g., braids per unit length) differing between the two sections. The flexibility of a braided or woven or mesh section depends, at least in part, upon the pattern density, with a more dense pattern being more rigid than a less dense pattern. In the illustrated embodiments, the first section 126a, 126b, 126c has a lower pattern density than the accompanying second section 128a, 128b, 128c, such that the first section is more flexible than the second section. By providing two different pattern densities, it will be seen that the flexibility of the urinary catheter body 124a, 124b, 124c varies along its length.

In the illustrated embodiment, each urinary catheter body 124a, 124b, 124c has only two braided or woven or mesh section, but other profiles are also within the scope of the present disclosure. For example, in a preferred embodiment, a urinary catheter body has five braided or woven or mesh sections, with three relatively rigid sections (i.e., sections having a relatively dense pattern) and two relatively flexible sections (i.e., sections with a relatively low pattern density). The relatively rigid and flexible sections alternate, with relatively rigid end sections, a relatively rigid midsection, and a relatively flexible section separating the midsection from each of the end sections. By such a configuration, the different sections of a urinary catheter formed with such a body will be positioned within the urethra as described above with respect to the five alternating-flexibility sections of the urinary catheter body 110 of FIG. 24 (i.e., with the more rigid sections in more linear portions of the urethra and the more flexible sections in more sharply curved portions of the urethra).

In the illustrated embodiment, each of the two sections has a generally uniform pattern density, such that the entire section has a generally uniform flexibility. In other embodiments, it is within the scope of the present disclosure for an individual braided or woven or mesh section to have a varying pattern density, such that the section itself has a varying flexibility. It is also within the scope of the present disclosure to provide a urinary catheter body having only one braided or woven or mesh section, which may define all or a portion of the length of the body. The material composition of the filaments of the braid or weave or mesh may also vary without departing from the scope of the present disclosure. By way of example, the filaments may be formed using polypropylene or PVC or polyurethane or another polymeric material. Other suitable materials may also be employed without departing from the scope of the present disclosure.

As in the embodiments discussed previously, an outer layer or sleeve or cover may be applied to the urinary catheter bodies 124a, 124b, and 124c of FIGS. 25-27 using any of a number of suitable of methods (including heat-shrinking or extrusion).

As already described, it should be understood that the above flexibility varying techniques are not exclusive of one another, and any two or more of the above flexibility varying techniques may be employed in combination without departing from the scope of the present disclosure.

Aspects of the present subject matter described above may be beneficial alone or in combination with one or more other aspects. Without limiting the foregoing description, in accordance with one aspect of the subject matter herein, there is provided a male urinary catheter having a proximal first section. A second section is adjacent to and distal from the proximal section. A third section is adjacent to and distal from the second section. A fourth section is adjacent to and distal from the third section. A fifth section is adjacent to and distal from the fourth section. The first, third, and fifth sections are relatively rigid and the second and fourth sections are relatively flexible.

In accordance with another aspect which may be used or combined with the preceding aspect, at least one of the second and fourth sections includes a spiral cut.

In accordance with another aspect which may be used or combined with the first aspect, the second and fourth sections include spiral cuts.

In accordance with another aspect which may be used or combined with any of the preceding two aspects, a chamfer is provided along at least a portion of the spiral cut.

In accordance with another aspect which may be used or combined with the first aspect, at least one of the second and fourth sections includes a coiled filament.

In accordance with another aspect which may be used or combined with the first aspect, the second and fourth sections include coiled filaments.

In accordance with another aspect which may be used or combined with the first aspect, at least one of the second and fourth sections includes at least one generally planar cut defining a bending point.

In accordance with another aspect which may be used or combined with the first aspect, the second and fourth sections each include at least one generally planar cut defining a bending point.

In accordance with another aspect which may be used or combined with the first aspect, at least one of the second and fourth sections is corrugated.

In accordance with another aspect which may be used or combined with the first aspect, the second and fourth sections are corrugated.

In accordance with another aspect which may be used or combined with the first aspect, the sections are defined by multifilament braids or weaves or meshes. The second and fourth sections have a lower pattern density than the first, third, and fifth sections.

In accordance with another aspect which may be used or combined with any of the preceding aspects, the flexibility of at least one of the second and fourth sections is substantially uniform along the length of that section.

In accordance with another aspect which may be used or combined with any of the first eleven aspects, the flexibility of at least one of the second and fourth sections varies along the length of that section.

In accordance with another aspect which may be used or combined with any of the preceding aspects, the sections are defined at least in part by an outer layer including cross-linking in the first, third, and fifth sections.

In accordance with another aspect, there is provided a method of deploying a urinary catheter within a male urethra. The method includes advancing the catheter through the urethra so as to position at least portions of relatively rigid proximal first and distal fifth sections of the catheter in the bladder and penis respectively. Second, third, and fourth sections of the catheter are positioned between the penis and the bladder, with the second and fourth sections being relatively flexible and separated by the relatively rigid third section.

In accordance with another aspect, there is provided a urinary catheter comprising a catheter body and an outer layer applied to the catheter body. The catheter body includes at least one generally planar cut defining a bending point.

In accordance with another aspect which may be used or combined with the preceding aspect, the catheter body includes a section having a plurality of generally planar cuts and the section has a substantially uniform flexibility along its length.

In accordance with another aspect which may be used or combined with the sixteenth aspect, the catheter body includes a section having a plurality of generally planar cuts and the section has a varying flexibility along its length.

In accordance with another aspect which may be used or combined with any of the preceding three aspects, the catheter body is formed by an injection molding procedure and the outer layer is extruded onto the catheter body.

In accordance with another aspect which may be used or combined with any of the sixteenth through eighteenth aspects, the catheter body is formed by an injection molding procedure and the outer layer is heat-shrunk onto the catheter body.

In accordance with another aspect which may be used or combined with any one of the preceding five aspects, a plurality of generally planar cuts define bending points, with at least one of the cuts defining a fluid pathway for fluid to enter into a hollow interior of the urinary catheter.

In accordance with another aspect, there is provided a urinary catheter having a catheter body and an outer layer applied to the catheter body. The catheter body includes at least one corrugated section.

In accordance with another aspect which may be used or combined with the preceding aspect, the corrugated section has a substantially uniform flexibility along its length.

In accordance with another aspect which may be used or combined with the twenty-second aspect, the corrugated section has a varying flexibility along its length.

In accordance with another aspect which may be used or combined with any of the preceding three aspects, the outer diameter of the outer layer is substantially uniform.

In accordance with another aspect, there is provided a urinary catheter having a catheter body and an outer layer applied to the catheter body. The catheter body includes at least one multifilament braid or weave or mesh.

In accordance with another aspect which may be used or combined with the preceding aspect, the multifilament braid or weave or mesh has a substantially uniform flexibility along its length.

In accordance with another aspect which may be used or combined with the twenty-sixth aspect, the multifilament braid or weave or mesh has a varying flexibility along its length.

In accordance with another aspect, there is provided a method of manufacturing a urinary catheter. A catheter body is formed by an injection molding procedure and an outer layer is extruded over at least a portion of the catheter body.

In accordance with another aspect, there is provided a method of manufacturing a urinary catheter. A tube is formed and at least a portion of the tube is covered with a stencil. A cross-linking operation is performed, thereby cross-linking only a portion of the tube not covered by the stencil, with the cross-linking operation being electro-polymerization or a chemical cross-linking operation.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A male urinary catheter, comprising:
an innermost body; and
an outermost layer applied to cover at least a portion of the body, wherein
the urinary catheter includes
a proximal first section configured to be at least partially positioned within a bladder when the urinary catheter is properly inserted within a male urethra
a second section adjacent to and distal from the proximal section and configured to be at least partially positioned within a relatively curved proximal portion of the male urethra when the urinary catheter is properly inserted within the male urethra,
a third section adjacent to and distal from the second section and configured to be at least partially positioned within a relatively less curved portion of the male urethra when the urinary catheter is properly inserted within the male urethra,
a fourth section adjacent to and distal from the third section and configured to be at least partially positioned within a relatively curved distal portion of the male urethra when the urinary catheter is properly inserted within the male urethra, and
a distal fifth section adjacent to and distal from the fourth section and configured to be at least partially positioned within a penis when the urinary catheter is properly inserted within the male urethra,
the second and fourth sections have a greater flexibility than the first section, the third section, and the fifth section,
the outermost layer is applied to cover the body in at least one of the first, third, and fifth sections and at least one of the second and fourth sections, with the outermost layer covering and directly contacting the entirety of an outer surface of the body in at least one of the sections, and
the difference between the flexibility of the second and fourth sections and the flexibility of the first section, the third section, and the fifth section is imparted by the body and/or the outermost layer.

2. The urinary catheter of claim 1, wherein the body includes a spiral cut in at least one of the second and fourth sections.

3. The urinary catheter of claim 1, wherein the body includes spiral cuts in the second and fourth sections.

4. The urinary catheter of claim 2, further comprising a chamfer along at least a portion of said spiral cut.

5. The urinary catheter of claim 1, wherein the body comprises a coiled filament in at least one of the second and fourth sections.

6. The urinary catheter of claim 1, wherein the body comprises coiled filaments in the second and fourth sections.

7. The urinary catheter of claim 1, wherein the body includes at least one generally planar cut defining a bending point in at least one of the second and fourth sections.

8. The urinary catheter of claim 1, wherein the body includes at least one generally planar cut defining a bending point in the second and fourth sections.

9. The urinary catheter of claim 1, wherein the body is corrugated in at least one of the second and fourth sections.

10. The urinary catheter of claim 1, wherein the body is corrugated in the second and fourth sections.

11. The urinary catheter of claim 1, wherein the body is defined by multifilament braids or weaves or meshes, with the body having a lower pattern density in the second and fourth sections than in the first, third, and fifth sections.

12. The urinary catheter of claim 1, wherein the flexibility of at least one of the second and fourth sections is substantially uniform along the length of that section.

13. The urinary catheter of claim 1, wherein the flexibility of at least one of the second and fourth sections varies along the length of that section.

14. The urinary catheter of claim 1, wherein the outermost layer includes cross-linking in the first, third, and fifth sections.

15. A method of deploying a urinary catheter having an innermost body and an outermost layer within a male urethra, comprising advancing the catheter through the urethra so as to position at least portions of proximal first and distal fifth sections of the catheter in the bladder and the penis respectively, wherein
 second, third, and fourth sections of the catheter are positioned between the penis and the bladder, with the second and fourth sections being separated by the third section and having a greater flexibility than the first section, the third section, and the fifth section,
 said outermost layer is applied to cover the body in at least one of the first, third, and fifth sections and at least one of the second and fourth sections, with the outermost layer covering and directly contacting the entirety of an outer surface of the body in at least one of the sections, and
 the difference between the flexibility of the second and fourth sections and the flexibility of the first section, the third section, and the fifth section is imparted by the body and/or the outermost layer.

16. A method of manufacturing a urinary catheter, comprising:
 forming an innermost catheter body by an injection molding procedure; and
 extruding an outermost layer over at least a portion of the catheter body, wherein
  the urinary catheter is manufactured to include
   a proximal first section configured to be at least partially positioned within a bladder when the urinary catheter is properly inserted within a male urethra,
   a second section adjacent to and distal from the proximal section and configured to be at least partially positioned within a relatively curved proximal portion of the male urethra when the urinary catheter is properly inserted within the male urethra,
   a third section adjacent to and distal from the second section and configured to be at least partially positioned within a relatively less curved portion of the male urethra when the urinary catheter is properly inserted within the male urethra,
   a fourth section adjacent to and distal from the third section and configured to be at least partially positioned within a relatively curved distal portion of the male urethra when the urinary catheter is properly inserted within the male urethra, and
   a distal fifth section adjacent to and distal from the fourth section and configured to be at least partially positioned within a penis when the urinary catheter is properly inserted within the male urethra,
  the second and fourth sections have a greater flexibility than the first section, the third section, and the fifth section,
  the outermost layer is applied to cover the catheter body in at least one of the first, third, and fifth sections and at least one of the second and fourth sections, with the outermost layer covering and directly contacting the entirety of an outer surface of the catheter body in at least one of said sections, and
  the difference in flexibility of the second and fourth sections and the flexibility of the first section, the third section, and the fifth section is imparted by the catheter body and/or the outermost layer.

17. The method of claim 16, wherein said forming an innermost catheter body by an injection molding procedure includes forming the catheter body so as to have a varying flexibility.

18. The method of claim 16, further comprising cross-linking only a portion of the outermost layer, thereby providing the outermost layer with a varying flexibility.

19. The method of claim 16, further comprising cross-linking a first portion of the outermost layer and cross-linking a second portion of the outermost layer to a lesser degree than the first portion, thereby providing the outermost layer with a varying flexibility.

\* \* \* \* \*